United States Patent
Wang et al.

(10) Patent No.: US 12,134,637 B2
(45) Date of Patent: Nov. 5, 2024

(54) MART-1(27-35) EPITOPE-SPECIFIC T CELL RECEPTOR

(71) Applicant: BGI SHENZHEN, Shenzhen (CN)

(72) Inventors: Fei Wang, Shenzhen (CN); Chengchi Chao, Shenzhen (CN); Bo Li, Shenzhen (CN); Yong Hou, Shenzhen (CN); Yuelu Yin, Shenzhen (CN); Shilei Wang, Shenzhen (CN); Kun Duan, Shenzhen (CN)

(73) Assignee: BGI SHENZHEN, Shenzhen (CN)

( * ) Notice: Subject to any disclaimer, the term of this patent is extended or adjusted under 35 U.S.C. 154(b) by 929 days.

(21) Appl. No.: 17/259,584

(22) PCT Filed: Jul. 12, 2018

(86) PCT No.: PCT/CN2018/095395
§ 371 (c)(1),
(2) Date: Jan. 12, 2021

(87) PCT Pub. No.: WO2020/010565
PCT Pub. Date: Jan. 16, 2020

(65) Prior Publication Data
US 2022/0340638 A1    Oct. 27, 2022

(51) Int. Cl.
*C07K 14/725* (2006.01)
*C12N 5/0783* (2010.01)
*C12N 5/10* (2006.01)
*C12N 15/867* (2006.01)

(52) U.S. Cl.
CPC ........ *C07K 14/7051* (2013.01); *C12N 5/0636* (2013.01); *C12N 5/10* (2013.01); *C12N 15/867* (2013.01); *C07K 2317/565* (2013.01)

(58) Field of Classification Search
CPC .......... C07K 14/7051; C07K 2317/565; C12N 5/0636; C12N 5/10; C12N 15/867; C12N 2740/16043; A61K 39/4611; A61K 39/4632; A61K 39/464491; A61P 35/00
See application file for complete search history.

(56) References Cited

U.S. PATENT DOCUMENTS

| | | | |
|---|---|---|---|
| 2009/0226404 A1 | 9/2009 | Schuler et al. | |
| 2010/0190163 A1* | 7/2010 | Sugiyama | A61P 35/02 |
| | | | 435/7.1 |
| 2019/0321401 A1* | 10/2019 | Goldfless | C07K 16/084 |

FOREIGN PATENT DOCUMENTS

| | | | | |
|---|---|---|---|---|
| CN | 101415827 A | 4/2009 | | |
| CN | 105821080 A | 8/2016 | | |
| CN | 106478809 A | 3/2017 | | |
| WO | 2008039818 A2 | 4/2008 | | |
| WO | 2008042814 A2 | 4/2008 | | |
| WO | WO-2009136874 A1 * | 11/2009 | ........... | A61K 39/292 |
| WO | 2017193104 A1 | 11/2017 | | |

OTHER PUBLICATIONS

Robbins et al., Single and dual amino acid substitutions in TCR CDRs can enhance antigen-specific T cell functions; 2008, J Immunol, 180 (9): 6116-6131. (Year: 2008).*
Wong et al., Comparative Analysis of the CDR loops of antigen receptors; 2019, Front. Immunol., 10(2454). (Year: 2019).*
International Search Report of PCT Application PCTCN2018095395 dated Mar. 27, 2019.
Written Opinion of International Searching Authority of PCT Application PCTCN2018095395 dated Mar. 27, 2019.

* cited by examiner

*Primary Examiner* — Daniel E Kolker
*Assistant Examiner* — James Ryland Melchior
(74) *Attorney, Agent, or Firm* — Pilloff Passino & Cosenza LLP; Rachel K. Pilloff; Sean A. Passino

(57) ABSTRACT

Provided is a MART-1 (27-35) epitope-specific T cell receptor, comprising an α chain and a β chain. The α chain comprises three complementary determining regions, respective sequences thereof being positions 61-66, positions 84-89, and positions 124-136 of SEQ ID No. 3. The β chain comprises three complementary determining regions, respective amino acid sequences thereof being positions 46-50, positions 68-73, and positions 112-125 of SEQ ID No. 4. A T cell expressing the TCR can effectively recognize a MART-1 (27-35) epitope polypeptide supported on a T2 cell and secrete IFN-γ, thereby demonstrating the functionality of the receptor. Use of the TCR with a relevant drug target allows for effective drug development.

19 Claims, 2 Drawing Sheets
Specification includes a Sequence Listing.

MART-1(27-35) EPITOPE-SPECIFIC T CELL RECEPTOR

TECHNICAL FIELD

The present disclosure relates to a MART-1 (27-35) epitope-specific T cell receptor.

BACKGROUND

Melanoma, also known as malignant melanoma, is a kind of malignant tumour derived from melanocytes, is often found in skin, and is also found in mucosa and ocular choroid, etc. Melanoma is the most malignant type in skin tumors, and is prone to distant metastasis. In Asians and people of color, melanoma originating from skin accounts for 50% to 70%. Excessive ultraviolet radiation is one of definite causes in Caucasians in Europe and America. Ultraviolet rays can cause skin burns and induce DNA mutations, thereby inducing development of melanoma. In addition, individuals with photosensitive skin, a large number of ordinary nevi or dysplastic nevi and skin cancer family history are all high-risk populations. Acral melanoma, which mostly occurs in Asia and Africa, is rarely exposed to ultraviolet radiation, and the cause thereof is still unclear.

In recent years, human melanoma-related antigens have been identified successively. MART-1 is a kind of melanoma-related antigen with a strong antigenicity, and the gene thereof has been cloned. The property of the antigen and an HLA molecule presenting the MART-1 has been partially illustrated. Studies have found that there are several immunodominant epitopes on the MART-1, which can induce CTL immune response in vivo and in vitro. The most common epitope is HLA-A*02 restricted epitope 27-35. Specific killer T cells (CTL) can be obtained by stimulating specific T cells against the epitope. This CTL can effectively kill tumour cells with positive MART-1 expression. However, at present, the clinical treatment effects for MART-1 (27-35) epitope is still very limited. The existing in vitro studies of clones of MART-1 specific CD8+T cells show that although genes of HLA-A*02 and MART-1 are expressed, only relatively few of epitopes are recognized by specific T cells. One of the important reasons is that the existing TCR of specific T cells corresponding to MART-1 can not recognize target cells of the MART-1 (27-35) epitope with high affinity. Therefore, it is of great significance to obtain a MART-1 (27-35) epitope-specific T cell receptor with high affinity.

CONTENT OF THE PRESENT INVENTION

An object of the present disclosure is to provide a MART-1 (27-35) epitope-specific T cell receptor. The sequence of the MART-1(27-35) epitope is as shown in SEQ ID No. 5.

The MART-1 (27-35) epitope-specific T cell receptor provided by the present disclosure comprises an α chain and a β chain. The α chain comprises three complementary determining regions, respective amino acid sequences thereof being positions 61-66, positions 84-89, and positions 124-136 of SEQ ID No. 3; or variants of the sequences with up to 3, 2, or 1 amino acid changes. The β chain comprises three complementary determining regions, respective amino acid sequences thereof being positions 46-50, positions 68-73, and positions 112-125 of SEQ ID No. 4; or variants of the sequences with up to 3, 2, or 1 amino acid changes.

Further, the amino acid sequence of a variable region of the α chain is positions 35-136 of SEQ ID No. 3; or variants of the sequences with up to 3, 2, or 1 amino acid changes; the amino acid sequence of a variable region of the β chain is positions 20-125 of SEQ ID No. 4; or variants of the sequences with up to 3, 2, or 1 amino acid changes.

The amino acid sequence of a constant region of the α chain is positions 148-288 of SEQ ID No. 3; and the amino acid sequence of a constant region of the β chain is positions 136-314 of SEQ ID No. 4.

Still further, the amino acid sequence of the α chain is specifically SEQ ID No. 3; and the amino acid sequence of the β chain is specifically SEQ ID No. 4.

A nucleic acid molecule encoding the T cell receptor also falls within the scope of protection of the present disclosure.

The nucleic acid molecule encoding the T cell receptor comprises a nucleic acid molecule encoding the α chain of the T cell receptor and the nucleic acid molecule encoding the β chain of the T cell receptor.

The sequences of nucleic acid molecules encoding the three complementary determining regions in the α chain of the T cell receptor are respectively positions 181-198, positions 250-267 and positions 370-408 of SEQ ID No. 1; or sequences having at least 99%, at least 95%, at least 90%, at least 85% or at least 80% identity with the sequences and encoding the same amino acid residues. The sequences of nucleic acid molecules encoding the three complementary determining regions in the β chain of the T cell receptor are respectively positions 136-150, positions 202-219 and positions 334-375 of SEQ ID No. 2; or sequences having at least 99%, at least 95%, at least 90%, at least 85% or at least 80% identity with the sequences and encoding the same amino acid residues.

Further, the sequence of the nucleic acid molecule encoding the variable region of the α chain is positions 103-408 of SEQ ID No. 1; or sequences having at least 99%, at least 95%, at least 90%, at least 85% or at least 80% identity with the sequences and encoding the same amino acid residues; the sequence of the nucleic acid molecule encoding the variable region of the β chain is positions 58-375 of SEQ ID No. 2; or sequences having at least 99%, at least 95%, at least 90%, at least 85% or at least 80% identity with the sequences and encoding the same amino acid residues.

Still further, the sequence of the nucleic acid molecule encoding the α chain is specifically SEQ ID No. 1; and the sequence of the nucleic acid molecule encoding the β chain is specifically SEQ ID No. 2.

An expression cassette, a vector or a cell containing the nucleic acid molecule also falls within the scope of protection of the present disclosure.

Further, the vector can be a retroviral vector, such as a lentiviral vector.

In an embodiment of the present disclosure, the vector is specifically obtained by linking the nucleic acid molecule encoding the α chain and the nucleic acid molecule encoding the β chain with a coding sequence of a linker peptide and then inserting it between restriction endonuclease cleavage sites, i.e., BamHI and SalI, of a lentiviral vector pRRLS-IN.cPPT.PGK-GFP.WPRE.

Further, the cell can be a T cell.

A pharmaceutical composition containing the vector or the cell also falls within the scope of protection of the present disclosure.

The pharmaceutical composition can be used for preventing and/or treating melanoma.

The use of the T cell receptor or the nucleic acid molecule or the vector or cell in preparing a drug for preventing and/or treating melanoma also falls within the scope of protection of the present disclosure.

The use of the T cell receptor or the nucleic acid molecule or the vector or cell in preventing and/or treating melanoma also falls within the scope of protection of the present disclosure.

The present disclosure also sets forth a method for preventing and/or treating melanoma. The method can comprise the following steps: using the T cell receptor or the nucleic acid molecule or the vector or cell as described above to prevent and/or treat melanoma.

DETAILED DESCRIPTION OF THE PREFERRED EMBODIMENT

Figure 1:
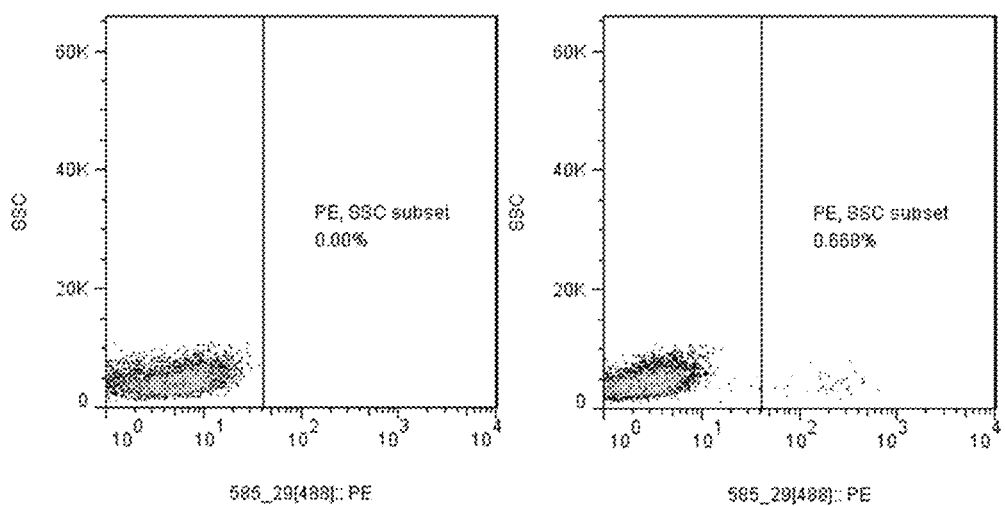
FIG. 1 shows the flow cytometry detection results after the first round stimulation by MART-1 (27-35) epitope polypeptide. The left plot is an unstimulated cell population of CD8-T; and the right plot is a flow cytometry cell population via tetramer detection after stimulation by MART-1 antigen.

The following examples facilitate a better understanding of the disclosure, but do not limit the disclosure. The experimental methods in the following examples are all conventional methods, unless otherwise specified. The test materials used in the following examples, unless otherwise specified, were purchased from general biochemical reagent stores. For the quantitative tests in the following examples, triplicates were set, and the results were averaged.

Experimental reagents and articles used in the following examples were as follows:

Experimental articles: blood collection tubes (including ACD anticoagulant), syringes, centrifuge tubes, 0.2 μm filtration membranes, MS separation columns, magnetic stands, and six-well plates with low adsorption; 0.2 μm filtration membranes, Dayou freezing kits and PCR tubes.

Experimental reagents: sterile saline solution (DPBS), RPMI1640 medium, Ficoll, AIM-V medium, sterile ultra-pure water (filtered through 0.1 um filtration membrane), MACS running buffer; AIM-V medium, GM-CSF, IL-4, IFN-γ, LPS and IL-7. Antigen-presenting beads, AIM-V medium, IL-21, IL-2 and IL-15. Sterile saline solution (PBS), Human IFN-γ ELISpot kits (MABTECH), tetramer (MART-1 antigen).

Example 1. Acquisition of Sequence of MART-1(27-35) Epitope-Specific T Cell Receptor with High Affinity I. Stimulation of MART-1 (27-35) Epitope-Specific T Cells 1. Isolation of PBMCs from Peripheral Blood of Healthy People 50 ml of blood samples were collected and centrifuged at room temperature at 100 g for 15 min; the plasma in the upper layer and the blood cells in the lower layer were collected, respectively. The plasma in the upper layer was centrifuged at room temperature at 1100 g for 20 min and the precipitate is discarded; after being inactivated at 56° C. (30 min), same was placed in a freezing layer of −20° C. and kept standing for 15 min. Centrifugation was performed at room temperature at 3800 rpm for 20 min. After centrifugation, the supernatant was human serum, which was taken for later use. The blood cells in the lower layer were made up to 50 ml with DPBS, and mixed upside down; 20 mL was pipetted to a 50 mL centrifuge tube; and 25 mL of blood sample after mixing homogeneously was carefully added on Ficoll and centrifuged at room temperature. After centrifugation, the liquid was divided into four layers, which, from top to bottom, were respectively a plasma layer, a buffy coat, a Ficoll layer and a blood cell layer; the buffy coat was carefully sucked out with a Pasteur dropper and transferred to a sterile centrifuge tube; 3 times the volume of 1640 medium was added therein to wash the sucked buffy coat, and the buffy coat was gently pipetted for several times, centrifuged at room temperature at 500 g for 10 min. The supernatant was carefully sucked out, and the precipitate is PBMC. DNAase was added therein to digest the agglomerate cells, and when the cells were judged to be a single cell suspension by eyes, 5-6 ml of MACS running buffer at 4° C. was added to terminate digestion. After termination, the single cell suspension was added onto a 70 μm cell sieve, and the tube and sieve were washed three times with 1-2 ml of MACS running buffer; and the single cell suspension was centrifuged at room temperature at 300 g for 10 min, and counted after resuspension.

2. Sorting of CD8$^+$ T Cell

After counting, PBMCs were added into MACS running buffer at 80 μl buffer/10$^7$ cells for resuspension, and 20 μl of CD8 beads/10$^7$ cells were added, mixed homogeneously, and incubated at 4° C. for 15 min; after incubation, 1-2 mL of buffer/10$^7$ cells were added for washing; the supernatant was completely sucked out, and the PBMCs were dispersed and 500 μl of buffer (0-10$^8$ total cells) was added for resuspension; and a separation column was placed on a magnetic stand and MACS running buffer was added to equilibrate the separation column. Cell suspension was added into (MS: 500 μl, LS: 3 mL), and the tube and separation column were washed with MACS running buffer for three times with the volume for each time being the same as above; after the column was removed, 1 ml of MACS running buffer was added, and then the plunger on the column was pushed vigorously, and the liquid that was pushed out is CD8$^+$ T cell, the cells were counted, and then cryopreserved at 10⁷/ml; and CD8⁻ T cells (negative cells) were adherent and DC cells (1.5-2 h or overnight) were obtained.

3. DC Loaded with MART-1 Polypeptide

Negative cells were resuspended in 5% human serum AIM-V, and plated; the petri dish was shaken to make the non-adherent cells resuspended in the supernatant. The supernatant was sucked out, and then AIM-V medium was added for drip washing; and the adherent cells were added into DC medium, after 48 h, half volume of 5% human serum AIM-V medium was supplemented; after 24 hours, the cells were purged with cold DPBS (the original culture medium and the cell fluid purged by subsequent addition of DPBS were separated in different tubes), and the cells were plated in a 12 well plate with $5\times10^5$ cells, with 1 ml of medium per well (the medium being 5% human serum AIM-V), and a cytokine was added therein to induce the maturation of DC cells. At the same time, the DC cells were loaded with the polypeptide (MART-1 (27-35) epitope peptide, SEQ ID No. 5) by adding the polypeptide into the cultured DC cells, and the cells were incubated at 37° C. for 16 h.

4. Co-Culture of DC Cells Loaded with the Polypeptide (MART-1 (27-35) Epitope Polypeptide) and CD8⁺ T Cells After 16 h, the DC cells loaded with the polypeptide (MART-1 (27-35) epitope polypeptide) were pipetted with cold DPBS and co-cultured with recovered CD8⁺ T; the CD8⁺ was purged, and the well plate was purged with AIM-V medium for at least 3 times, and centrifuged at room temperature at 400 g for 5 min; the cells were resuspended with 1 ml of AIM-V, DNAase was added to digest same into a single-cell suspension, after 0-5 min, the reaction was terminated by adding 5 ml of AIM-V, and centrifugation was carried out at room temperature at 400 g for 5 min; and T cells were resuspended with 5% human serum AIM-V, and were plated at $6.25\times10^5$ cells/cm². The DC cells loaded with the polypeptide (MART-1 (27-35) epitope polypeptide) were added in a proportion and IL-21 was added; 72 h after addition, medium supplement or half volume-medium exchange was carried out every 2-3 days, and the total volume of cytokines of IL 2, IL-7 and IL-15 were supplemented; and cytokines were supplemented or medium were exchanged every 2-3 days. On day 5 of culturing, antigen-presenting beads used for the second round of stimulation were prepared: on day 1, the total number of magnetic beads required was calculated, and the required volume of magnetic beads was taken out and performed adsorption with magnet to remove the supernatant. The same volume of a boric acid solution was added for washing twice, and then the same volume of the solution was added again for resuspension. CD28 and HLA-A2: Ig were added, and same was placed onto a shaker at 4° C. overnight. On day 10 of culturing, the cells were resuspended, and the cells used for detection and flow cell sorting was taken out, and the remaining cells were used for the second round of co-culture.

II. Single-Cell TCR Sequencing for MART-1 (27-35) Epitope-Specific T Cells

1. Synthesis of HLA-A*02 Tetramer Loaded with MART-1 (27-35) Epitope Polypeptide A tetramer is formed by connecting four monomers. A complex formed by a single HLA molecular protein and a polypeptide is referred to as a monomer. The tetramer is formed by connecting the four monomers via biotin-streptavidin. Monomer substitution refers to the process of polypeptide exchange on a monomer. Due to different experimental needs, tetramers need to be constructed for different antigens. The substitution of different antigens (polypeptide sequences) is referred to as monomer substitution.

5 μl of 10 mM MART-1 (27-35) epitope peptide (SEQ ID No. 5) was taken, and 120 μl of PBS was added therein, and placed same on ice; 20 μl of the diluted polypeptide of interest and HLA-A*02 monomer were added to the 96-well plate with a U-shaped bottom, and mixed homogeneously; the plate is sealed with tinfoil, and the reaction solution was added to the bottom of the plate; the crosslinking was performed under UV lamp at 365 nm for 30 min, and incubated at 37° C. in the dark for 30 min; and 30 μl of MART-1 (27-35) epitope polypeptide was used to substitute HLA-A*02 monomer on anew plate, and 3.3 μl of fluorescence-conjugated streptavidin was added, and placed same on ice for 30 min; and a stop solution was prepared during the incubation on ice; after staying overnight at 4° C. or staying on ice in dark for 30 min, the stop solution was stored at 4° C. for later use.

2. Flow Cytometry Detection of MART-1(27-35) Epitope-Specific T Cell Receptor

The stimulated cells in step I-4 were resuspended and counted. The cells used for flow cell sorting was taken out at $2\times10^5$/tube, and then 1 ml of PBS was added therein for resuspension. After centrifugation at 4° C. at 500 g for 5 min, the supernatant was carefully discarded and 200 μl of PBS was added for resuspension. The tetramer (10 μl/ml) prepared in step 1 was added to the tube, mixed homogeneously and carried out a reaction at 4° C. for 30 min. After the reaction time is over, 1 ml of PBS was added for resuspension and centrifugation was carried out at 4° C. at 500 g for 5 min. The supernatant was carefully discarded, and 200 μl of PBS was added for resuspension, and it was placed on ice for flow cytometry detection. After flow cytometry loading, positive population was selected to sort single cells.

The flow cytometry detection results after the first round stimulation by MART-1 (27-35) epitope polypeptide were as shown in FIG. 1. It can be seen therefrom that compared with the control group, of which T cells without stimulation were cultured under the same conditions, the T cells after stimulation by MART-1 (27-35) epitope polypeptide antigen can be detected 0.668% of positive tumour-specific T cells by the tetramer.

Figure 2:
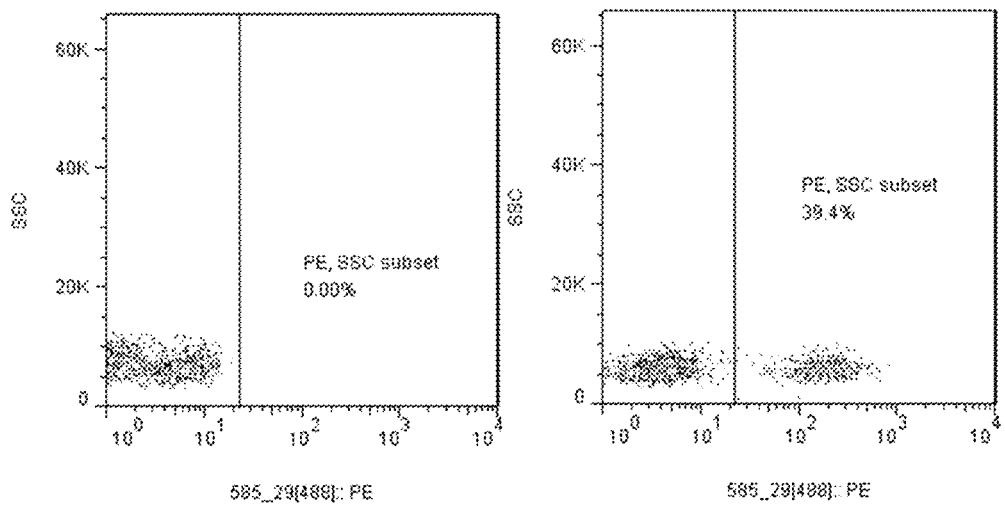
FIG. 2 shows the flow cytometry detection results after the second round stimulation by MART-1 (27-35) epitope polypeptide. The left plot is an unstimulated cell population of CD8-T; and the right plot is a flow cytometry cell population via tetramer detection after stimulation by MART-1 antigen.

The flow cytometry detection results after the second round stimulation by MART-1 (27-35) epitope polypeptide were as shown in FIG. 2. It can be seen therefrom that compared with the control group, of which T cells without the first round and the second round of stimulation were cultured under the same conditions, the proportion of positive tumour-specific T cells in T cells after stimulation by MART-1 (27-35) epitope polypeptide antigen that can be detected by the tetramer increased greatly, and reached to 39.4%.

3. Elispot Detection of MART-1(27-35) Epitope Polypeptide-Specific T Cell

Preparation of target cells: T2 cells were counted, and the required cells were taken out. After centrifugation at room temperature at 400 g for 5 min, the cells were resuspended in serum-free IMDM medium.

Loading target cells with MART-1 (27-35) epitope polypeptide: a appropriate well plate and a loading volume were determined according to the number of cells taken out; the MART-1 (27-35) epitope polypeptide was prepared into 10 μg/μl, added at 1000× to the loading volume, resuspended and mixed homogeneously, and incubated in a 5% $CO_2$ incubator at 37° C. for 4 h. At the same time, a control group loaded with an unrelated polypeptide was set up.

Preparation of effector cells (MART-1 (27-35) epitope polypeptide-specific T cell screened out by flow cytometry after the second round of stimulation): the effector cells were counted, and the required cells were taken out, centrifuged at room temperature at 300 g for 10 min, and then resuspended with 5% of human serum AIM-V medium, and it was placed on ice.

Washing the plate: when 45 min was left for antigen loading, the reaction well plate in the human IFN-γ ELISpot kit was taken out from the super clean bench, PBS was added therein, and the liquid in the wells was patted off after standing for 30 s. The pat action was repeated five times, and then 10% FBS RPMI1640 medium was added at 100 µl/well, and incubated in a 5% CO$_2$ incubator at 37° C. for 30 min.

Figure 3:
FIG. 3 shows the Elispot detection results of MART-1 (27-35) epitope polypeptide-specific T cell. 7 holes, from left to right, sequentially represent T+T2+an effective polypeptide, T+T2+an unrelated polypeptide, T+T2, T+an effective peptide, T+an unrelated peptide, T, and T+OKT3.

Addition of sample: after the time for antigen loading is over, T2 cells in the well plate were purged with 5% human serum AIM-V medium, and centrifuged at room temperature at 400 g for 5 min, and resuspended with 5% human serum AIM-V medium. The effector cells were added into the reaction well plate at 50 µl/well, then the target cell suspension was added at 50 µl/well, and the reaction well plate was put into a 5% CO$_2$ incubator at 37° C. for culturing 16-48 h. After the culture time is over, PBS was added at 150 µl/well, and the liquid in the wells was patted off after standing for 30 s. The pat action was repeated five times, and an anti-human IFN-γ detection antibody solution (7-b6-1-ALP) was prepared with PBS containing 0.5% FBS (filtered by a 0.2 µm filter membrane). After adding 200× of 7-b6-1-ALP antibody and mixing with PBS containing 0.5% FBS thoroughly, it was added into the reaction well plate at 100 µl/well. The reaction plate was put into a 5% CO$_2$ incubator at 37° C. for reacting 2 h. After the reaction time is over, PBS was added at 150 µl/well, and the liquid in the wells was patted off after standing for 30 s. The pat action was repeated five times, and NBT/BCIP (filtered by a 0.2 µm filter membrane) was added to the reaction well at 100 µl/well in the dark. The wells were color developed in the dark for 30 s-5 min (taking the observed obvious positive control spots as the reaction end point) and then washed with a large amount of tap water, and the results were observed after drying. As shown in FIG. 3, compared with the control group (T+T2+the unrelated polypeptide, T+T2, T+the effective polypeptide, T+the unrelated polypeptide and T are five negative control groups under the same conditions, and T+OKT3 is the positive control group; wherein OKT3 is an anti-CD3 antibody, and the reaction of OKT3 with T cells can promote T cells to secrete IFN-γ and produces spots in the color development reaction, and OKT3 can be used as a positive control), the MART-1 (27-35) epitope polypeptide-specific T cells can effectively recognize the polypeptide loaded with T2 (target cells) and secrete IFN-γ, proving that such population of cells are functional.

4. Single-Cell TCR Sequencing

The reagents used are as shown in Table 1.

TABLE 1

Reagents required for full-length sequencing of single-cell TCR

| M0314L | Rnase Inhibitor, Murine | NEB |
| T8787 | Triton x-100 | SIGMA |
| 4030 | dNTP Mixture | TAKARA |
| 18064071 | SuperScript II Reverse Transcriptase | Invitrogen |
| B0300-1VL | Betaine solution | SIGMA |
| 20-303 | MgC12 | MILLIPORE |
| KK2602 | KAPA HiFi HotStart ReadyMix | KAPA BIOSYSTEMS |
| AM9938 | Nuclease-free Water | AMBION |

TABLE 1-continued

Reagents required for full-length sequencing of single-cell TCR

| B7022S | Gel Loading dye, Orange | NEB |
| MD 109-2 | l00bp DNA ladder | TIANGEN |

The primer sequences used are as shown in Table 2.

TABLE 2

Primers required for full-length sequencing of single-cell TCR of MART-1 (27-35) epitope-specific T cells

| α or β chain | Primer name | Sequence (5'-3') | Tm/° C. | GC % |
|---|---|---|---|---|
| TCRA | Outer | GCAGACAGACTTGTCACTGG (SEQ ID No. 7) | 59.1 | 55 |
|  | Middle | TGGATTTAGAGTCTCTCAGCT GGTACACG (SEQ ID No. 8) | 66.1 | 48.3 |
|  | Inner | GGTACACGGCAGGGTCAGGGT TC (SEQ ID No. 9) | 67.6 | 65.2 |
| TCRB | Outer | TGGTCGGGGAAGAAGCCTGTG (SEQ ID No. 10) | 63.4 | 65 |
|  | Middle | TCTGCTTCTGATGGCTCAAAC ACAGC_ (SEQ ID No. 11) | 66.3 | 50 |
|  | Inner | TTCTGATGGCTCAAACACAGC GA (SEQ ID No. 12) | 63.5 | 47.8 |

(1) Cell lysis

A mixed solution for cell lysis was prepared according to Table 3.

TABLE 3

Mixed solution for cell lysis

| Mixed solution for cell lysis | Volume µl | Final concentration |
|---|---|---|
| RNase/DNase-free water | 1.86 |  |
| 10 µM Oligo-dT Primer | 1 | 2.5 µM |
| 10 mM dNTP | 1 | 2.5 mM |
| 40 U/µl RNase Inhibitor | 0.1 | 2 U/µl |
| 10% Triton X-100 | 0.04 | 0.2% |
| Total volume | 4 |  |

When preparing, the preparation was carried out according to 110% of the number of samples (if there were 10 cell samples, 11 tubes were prepared). The prepared lysate was pipetted, mixed homogeneously, and then subpackaged to clean PCR tubes for centrifugation at 4° C. at 14000 rpm for 30 s (droplets were centrifuged to the bottom of the tube and bubbles were removed); the PCR tubes were placed in an ice box for subsequent dividing the lysate into cells; positive population (i.e., the MART-1 (27-35) epitope-specific T cells obtained in step 7) was selected and single cells were divided into the PCR tubes containing the lysate. After sorting, the tube cap was closed for short-term centrifugation, and the PCR instrument was adjusted for single cell lysis.

0.2 ml PCR tubes were placed in a PCR instrument, incubated at 72° C. for 3 min (if the cells were bulk samples, increasing to 5 min), and the temperature of the hot lid was 75° C. After the lysis, the PCR tubes were immediately placed on ice for 1 min; and centrifugated at 4° C. at 10000 rpm for 30 s, and then immediately transferred to ice. After this step, all the mRNAs were released from the single cells, and Oligo-dT primers were also bound to the mRNAs.

(2) Preparation of reverse transcription system, according to Table 4.

TABLE 4

Reverse transcription system

| Ingredient | Volume μl | Final concentration |
| --- | --- | --- |
| 5 × SuperScript II | 2 | 1× |
| 5M Betaine | 2 | 1M |
| 100 mM MgCl$_2$ | 0.9 | 9 mM |
| 100 mM DTT | 0.25 | 2.5 mM |
| 100 μM TSO | 0.1 | 1 μM |
| 40 U/ul RNAse inhibitor | 0.25 | 1 U/μL |
| 200 U/μl SSII | 0.5 | 10 U/μL |
| Total volume | 6 | |

When preparing, the preparation was carried out according to the number of samples+0.5 (if there were 9 cell samples, 9.5 tubes were prepared). The prepared Mix was mixed thoroughly, and then sequentially added into the centrifuge tubes in the previous step;

and (3) after pipetting, mixing homogeneously and fast centrifuging, a reverse transcription reaction (75° C. hot lid) was carried out according to the conditions as shown in Table 5.

TABLE 5

Reverse transcription reaction conditions

| Cycle | Temperature | Time |
| --- | --- | --- |
| 1 | 42° C. | 90 min |
| 10 | 50° C. | 2 min |
|  | 42° C. | 2 min |
| 1 | 70° C. | 15 min |
| 1 | 4° C. | forever |

After this step, the first strand cDNAs of all mRNAs were synthesized;

and (4) the first round of PCR Mix was prepared according to Table 6.

TABLE 6

First round of PCR Mix

| Ingredient | Volume μl | Final concentration |
| --- | --- | --- |
| 2 × KAPAHiFi HotStart Ready Mix | 12.5 | 1× |
| IS PCR Primer (10 μM) | 1 | 0.4 μM |
| TCRA-out Primer (10 μM) | 0.5 | 0.2 μM |
| TCRB-out Primer (10 μM) | 0.5 | 0.2 μM |
| NF-water | 0.5 | |
| Total volume | 15 | |

When preparing, the preparation was carried out according to the number of samples+0.5 (if there were 9 cell samples, 9.5 tubes were prepared). The prepared Mix was mixed thoroughly, and 15 μl of the prepared Mix was sequentially added into the centrifuge tubes in the previous step. After pipetting, mixing homogeneously and fast centrifuging, pre-amplification was performed according to the conditions as shown in Table 7.

TABLE 7

Pre-amplification conditions for first round of PCR

| Cycle | Temperature | Time |
| --- | --- | --- |
| 1 | 95° C. | 3 min |
| 25 | 98° C. | 20 s |
|  | 55° C. | 15 s |
|  | 72° C. | 2 min |
| 1 | 72° C. | 5 min |
| 1 | 4° C. | forever |

(5) The second round of PCR Mix was prepared according to Table 8.

TABLE 8

Second round of PCR Mix

| Ingredient | Volume μl | Final concentration |
| --- | --- | --- |
| 2 × KAPAHiFi HotStart Ready Mix | 12.5 | 1× |
| IS PCR Primer (10 μM) | 1 | 0.4 μM |
| TCRA-middle Primer (10 μM) | 0.5 | 0.2 μM |
| TCRB-middle Primer (10 μM) | 0.5 | 0.2 μM |
| NF-water | 9.5 | |
| Total volume | 24 | |

When preparing, the preparation was carried out according to the number of samples+0.5 (if there were 9 cell samples, 9.5 tubes were prepared). The prepared Mix was mixed thoroughly, and 24 μl of the prepared Mix was sequentially added into the centrifuge tubes in the previous step. After pipetting, mixing homogeneously and fast centrifuging, pre-amplification was performed according to the conditions as shown in Table 9.

TABLE 9

Pre-amplification conditions for second round of PCR

| Cycle | Temperature | Time |
| --- | --- | --- |
| 1 | 95° C. | 3 min |
| 25 | 98° C. | 20 s |
|  | 60° C. | 15 s |
|  | 72° C. | 2 min |
| 1 | 72° C. | 5 min |
| 1 | 4° C. | forever |

(6) The third round of PCR Mix was prepared according to Table 10.

TABLE 10

Third round of PCR Mix

| Ingredient | Volume μl | Final concentration |
| --- | --- | --- |
| 2 × KAPAHiFi HotStart Ready Mix | 12.5 | 1× |
| IS PCR Primer (10 μM) | 1 | 0.4 μM |
| TCRA-in Primer (10 μM) | 0.5 | 0.2 μM |
| TCRB-in Primer (10 μM) | 0.5 | 0.2 μM |
| NF-water | 9.5 | |
| Total volume | 24 | |

When preparing, the preparation was carried out according to the number of samples+0.5 (if there were 9 cell samples, 9.5 tubes were prepared). The prepared Mix was mixed thoroughly, and 24 μl of the prepared Mix was sequentially added into the centrifuge tubes in the previous step. After pipetting, mixing homogeneously and fast centrifuging, pre-amplification was performed according to the conditions as shown in Table 11.

TABLE 11

Pre-amplification conditions for third round of PCR

| Cycle | Temperature | Time |
|---|---|---|
| 1 | 95° C. | 3 min |
| 35 | 98° C. | 20 s |
|  | 60° C. | 15 s |
|  | 72° C. | 2 min |
| 1 | 72° C. | 5 min |
| 1 | 4° C. | forever |

(7) Electrophoresis detection: After completion of PCR, electrophoresis detection was performed, wherein 2% agarose gel was used, 15 µL of the product was taken and mixed homogeneously with 3 ul of Loading buffer, electrophoresis was performed at 130 V for 45 min, and the target band was recovered by gel cutting. The target band was then linked to a T vector, and the colony PCR identification was carried out.

Figure 4:
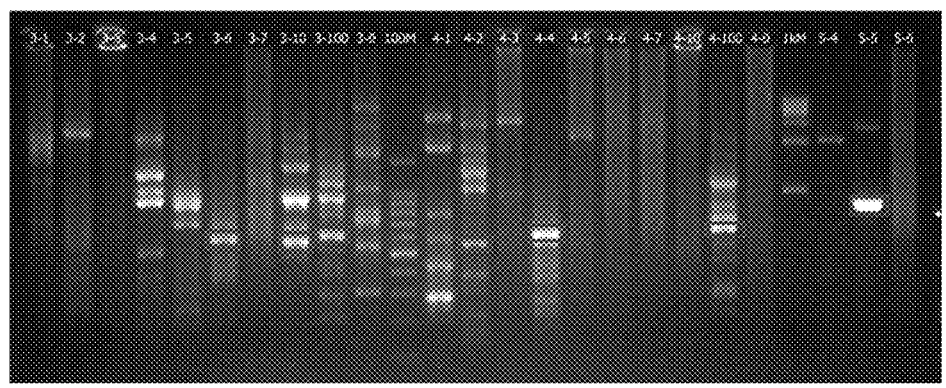
FIG. 4 is an amplification electropherogram of a single cell TCR. The bands marked by a frame are subjected to enzyme digestion and gel recovery.
Figure 5:
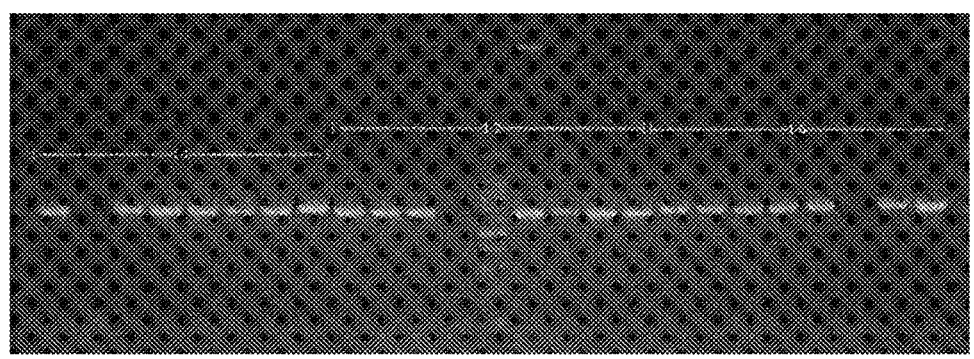
FIG. 5 is an electrophoretogram of products obtained after colony PCR of a TA clone. 1-1 represents TA cloning performed by one clone, 1-2 represents TA cloning performed by another clone, and 1-6 represents TA cloning performed by yet another clone.

FIG. 4 is an amplification electropherogram of a single cell TCR. FIG. 5 is a colony PCR electrophoretogram of a TA clone. The results in the figures show that the amplified TCR fragments were successfully linked to the T vector, and the insert fragment vector constructed successfully can be effectively detected by colony PCR.

(8) The sequenced fragments were blasted on the IMGT website, and respectively spliced with the C region of TCR α and TCR β chains to form a complete set of TCR sequences.

III. Screening and Functional Verification of MART-1 (27-35) Epitope-Specific TCR Sequences The set of single-cell TCR sequences of MART-1 (27-35) epitope-specific T cells obtained in step II were in the order of abundance from high to low. The sequences with a high abundance were selected, and then the top 5% of the sequences after ordering according to the abundance from high to low were subjected to preliminary functional verification to determine the final full-length TCR sequences for treatment. Among them, a functional paired TCR α/β sequences (labeled clone #4) with abundance reaching 1.5%, after the start codon thereof was found, were spliced according to the actual sequence of the constant region (TRAC/TRBC) to form a new sequence, in which, the sequence of the complete coding gene of the α chain was SEQ ID No. 1 (encoding the α chain as shown in SEQ ID No. 3), and the sequence of the complete coding gene of the β chain was SEQ ID No. 2 (encoding the β chain as shown in SEQ ID No. 4). The positions 103-408 of SEQ ID No. 1 were the coding genes of the α chain variable region (positions 181-198, positions 250-267 and positions 370-408 were the coding genes of three CDRs, respectively), and positions 58-375 of SEQ ID No. 2 were the coding genes of the β chain variable region (positions 136-150, positions 202-219 and positions 334-375 were the coding genes of three CDRs, respectively).

Figure 6:
FIG. 6 is a schematic diagram of part of the structure of a recombinant viral vector.

According to the schematic diagram as shown in FIG. 6, the coding genes of the α chain and β chain as shown in SEQ ID No. 1 and SEQ ID No. 2 were linked by the gene sequence of P2A peptide and then constructed into a lentiviral vector pRRLSIN.cPPT.PGK-GFP.WPR to obtain a recombinant viral vector. The structure of the recombinant viral vector was described as follows: the DNA fragment as shown in SEQ ID No. 6 was inserted into the intermediate position of BamHI and SalI double restriction endonuclease sites of pRRLSIN.cPPT.PGK-GFP.WPRE vector, and then a recombinant plasmid was obtained.

Figure 7:
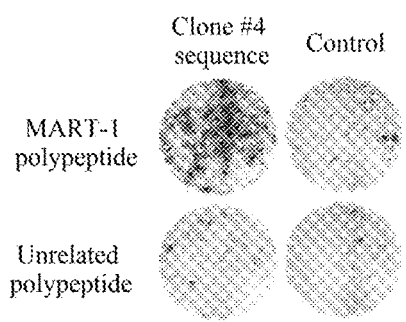
FIG. 7 shows the Elispot detection results of MART-1 (27-35) epitope polypeptide-specific T cell corresponding to clone #4 sequence.

The constructed recombinant viral vector was used to infect T cells, and then Elispot detection was carried out according to the method in step I-5 to verify the function thereof. Results were as shown in FIG. 7. Compared with the GFP control experimental group, the virus-infected T cells constructed by clone #4 sequence can effectively recognize the MART-1 (27-35) epitope polypeptide loaded by T2 and secrete IFN-γ, i.e., can effectively react with target cells.

INDUSTRIAL APPLICATIONS

In the present disclosure, a specific T cell population is obtained by stimulating specific T cells with MART-1 (27-35) epitope in vitro, and sets of TCR sequences of effective T lymphocytes corresponding to MART-1 (27-35) epitope is obtained by using single cell pairing TCR sequencing technology, and the sets of sequences are in the order of abundance for in vitro function verification, and finally the TCR claimed by the present disclosure is obtained. Experiments have proved that the T cell expressing the TCR provided by the present disclosure can effectively recognize MART-1 (27-35) epitope polypeptide loaded by T2 cells (target cells) and secrete IFN-γ, thereby proving that such population of T cells are functional. Effective TCR can be used for adoptive cellular immunotherapy. In addition, the sets of sequenced in combination with affinity enhancement or related drug targets can effectively used for drug development and have broad market prospects.

SEQUENCE LISTING

The instant application contains a Sequence Listing which is being submitted in ASCII format via EFS-WEB and is hereby incorporated by reference in its entirety.
File name: 5_SQLv2.txt
Creation date: Aug. 3, 2021
Modified: Sep. 17, 2021
Byte size: 12,354 bytes

What is claimed is:

1. A MART-1 (27-35) epitope-specific T cell receptor, comprising an α chain and a β chain;
   the α chain comprises three complementary determining regions, respective amino acid sequences thereof being the amino acid sequences of positions 61-66, positions 84-89, and positions 124-136 of SEQ ID No. 3; and
   the β chain comprises three complementary determining regions, respective amino acid sequences thereof being the amino acid sequences of positions 46-50, positions 68-73, and positions 112-125 of SEQ ID No. 4.

2. The T cell receptor as defined in claim 1, wherein: the amino acid sequence of a variable region of the α chain is the amino acid sequence of positions 35-136 of SEQ ID No. 3; and
   the amino acid sequence of a variable region of the β chain is the amino acid sequence of positions 20-125 of SEQ ID No. 4.

3. The T cell receptor as defined in claim 1, wherein:
   the amino acid sequence of a constant region of the α chain is positions 148-288 of SEQ ID No. 3; and the amino acid sequence of a constant region of the β chain is positions 136-314 of SEQ ID No. 4.

4. The T cell receptor as defined in claim 1, wherein:
   the amino acid sequence of the α chain is SEQ ID No. 3; and the amino acid sequence of the β chain is SEQ ID No. 4.

5. A nucleic acid molecule encoding the T cell receptor as defined in claim 1.

6. The nucleic acid molecule as defined in claim 5, wherein: the nucleic acid molecule encoding the T cell receptor comprises a nucleic acid molecule encoding the α chain of the T cell receptor and the nucleic acid molecule encoding the β chain of the T cell receptor;
   the sequences of nucleic acid molecules encoding the three complementary determining regions in the α chain of the T cell receptor are respectively the sequences of nucleic acid of positions 181-198, positions 250-267 and positions 370-408 of SEQ ID No. 1; and the sequences of nucleic acid molecules encoding the three complementary determining regions in the β chain of the T cell receptor are respectively the sequences of nucleic acid of positions 136-150, positions 202-219 and positions 334-375 of SEQ ID No. 2.

7. The nucleic acid molecule as defined in claim 5, wherein: the sequence of the nucleic acid molecule encoding the variable region of the α chain is the sequence of nucleic acid of positions 103-408 of SEQ ID No. 1; and the sequence of the nucleic acid molecule encoding the variable region of the β chain is the sequence of nucleic acid of positions 58-375 of SEQ ID No. 2.

8. The nucleic acid molecule as defined in claim 5, wherein: the sequence of the nucleic acid molecule encoding the α chain is SEQ ID No. 1; and the sequence of the nucleic acid molecule encoding the β chain is SEQ ID No. 2.

9. A cell containing the nucleic acid molecule as defined in claim 5.

10. The cell as defined in claim 9, wherein: the cell is a T cell.

11. A pharmaceutical composition containing the cell as defined in claim 9.

12. An expression cassette containing the nucleic acid molecule as defined in claim 5.

13. A vector containing the nucleic acid molecule as defined in claim 5.

14. The vector as defined in claim 13, wherein: the vector is obtained by linking the nucleic acid molecule encoding the a chain and the nucleic acid molecule encoding the 6 chain with a coding sequence of a linker peptide and then inserting between BamHI and SalI of a lentiviral vector pRRLSIN.cPPT.PGK-GFP.WPRE.

15. A pharmaceutical composition containing the vector as defined in claim 13.

16. A method for treating melanoma, comprising the following steps: administering to a subject in need thereof a therapeutically effective amount of the T cell receptor according to claim 1.

17. A method for treating melanoma, comprising the following steps: administering to a subject in need thereof a therapeutically effective amount of the nucleic acid molecule according to claim 5.

18. A method for treating melanoma, comprising the following steps: administering to a subject in need thereof a therapeutically effective amount of the cell according to claim 9.

19. A method for treating melanoma, comprising the following steps: administering to a subject in need thereof a therapeutically effective amount of the vector according to claim 13.

* * * * *

SEQUENCE LISTING

<160> NUMBER OF SEQ ID NOS: 12

<210> SEQ ID NO 1
<211> LENGTH: 867
<212> TYPE: DNA
<213> ORGANISM: Artificial Sequence
<220> FEATURE:
<223> OTHER INFORMATION: MART-1 (27-35) epitope-specific T cell receptor
      alpha chain

<400> SEQUENCE: 1

```
atgcctgcag gtcgacgatt aagcagtggt atcaacgcag agtacgggga gagtttact    60
agtgatcctg tggcttcagt tgagctgaga gtttggagcc aacagaagga ggtggagcag   120
aattctggac ccctcagtgt tccagaggga gccattgcct ctctcaactg cacttacagt   180
gaccgaggtt cccagtcctt cttctggtac agacaatatt ctgggaaaag ccctgagttg   240
ataatgttca tatactccaa tggtgacaaa gaagatggaa ggtttacagc acagctcaat   300
aaagccagcc agtatgtttc tctgctcatc agagactccc agcccagtga ttcagccacc   360
tacctctgtg ccgtgaacac ccccatgaaa tatggaaaca aactggtctt tggcgcagga   420
accattctga gagtcaagtc ctatatccag aaccctgacc ctgccgtgta ccagctgaga   480
gactctaaat ccagtgacaa gtctgtctgc ctattcaccg attttgattc tcaaacaaat   540
gtgtcacaaa gtaaggattc tgatgtgtat atcacagaca aaactgtgct agacatgagg   600
tctatggact tcaagagcaa cagtgctgtg gcctggagca caaatctga ctttgcatgt    660
gcaaacgcct tcaacaacag cattattcca gaagacacct tcttccccag cccagaaagt   720
tcctgtgatg tcaagctggt cgagaaaagc tttgaaacag atacgaacct aaactttcaa   780
aacctgtcag tgattgggtt ccgaatcctc ctcctgaaag tggccgggtt taatctgctc   840
atgacgctgc ggctgtggtc cagctag                                       867
```

<210> SEQ ID NO 2
<211> LENGTH: 945
<212> TYPE: DNA
<213> ORGANISM: Artificial Sequence
<220> FEATURE:
<223> OTHER INFORMATION: MART-1 (27-35) epitope-specific T cell receptor beta chain

<400> SEQUENCE: 2

```
atgggcacca ggctcctctg ctgggtggtc ctgggttttcc tagggacaga tcacacaggt   60
gctggagtct cccagtcccc taggtacaaa gtcgcaaaga gaggacagga tgtagctctc   120
aggtgtgatc caatttcggg tcatgtatcc cttttttggt accaacaggc cctggggcag   180
ggccagagt tctgacttta tttccagaat gaagctcaac tagacaaatc ggggctgccc   240
agtgatcgct tctttgcaga aaggcctgag ggatccgtct ccactctgaa gatccagcgc   300
acacagcagg aggactccgc cgtgtatctc tgtgccagca gctacgtagt gggactgacc   360
tacaatgagc agttcttcgg gccagggaca cggctcaccg tgctagagga cctgaaaaac   420
gtgttcccac ccgaggtcgc tgtgtttgag ccatcagaag cagagatctc ccacacccaa   480
aaggccacac tggtgtgcct ggccacaggc ttctacccg accacgtgga gctgagctgg   540
tgggtgaatg ggaaggaggt gcacagtggg gtcagcacag acccgcagcc cctcaaggag   600
cagcccgccc tcaatgactc cagatactgc ctgagcagcc gctgagggt ctcggccacc    660
ttctggcaga accccgcaa ccacttccgc tgtcaagtcc agttctacgg gctctcggag    720
aatgacgagt ggacccagga tagggccaaa cctgtcaccc agatcgtcag cgccgaggcc   780
tggggtagag cagactgtgg cttcacctcc gagtcttacc agcaagggg cctgtctgcc   840
accatcctct atgagatctt gctagggaag gccaccttgt atgccgtgct ggtcagtgcc   900
ctcgtgctga tggccatggt caagagaaag gattccagag gctag                   945
```

<210> SEQ ID NO 3
<211> LENGTH: 288

```
<212> TYPE: PRT
<213> ORGANISM: Artificial Sequence
<220> FEATURE:
<223> OTHER INFORMATION: MART-1 (27-35) epitope-specific T cell receptor
      alpha chain

<400> SEQUENCE: 3

Met Pro Ala Gly Arg Arg Leu Ser Ser Gly Ile Asn Ala Glu Tyr Gly
1               5                   10                  15

Glu Ser Phe Thr Ser Asp Pro Val Ala Ser Val Glu Leu Arg Val Trp
            20                  25                  30

Ser Gln Gln Lys Glu Val Glu Gln Asn Ser Gly Pro Leu Ser Val Pro
        35                  40                  45

Glu Gly Ala Ile Ala Ser Leu Asn Cys Thr Tyr Ser Asp Arg Gly Ser
    50                  55                  60

Gln Ser Phe Phe Trp Tyr Arg Gln Tyr Ser Gly Lys Ser Pro Glu Leu
65                  70                  75                  80

Ile Met Phe Ile Tyr Ser Asn Gly Asp Lys Glu Asp Gly Arg Phe Thr
                85                  90                  95

Ala Gln Leu Asn Lys Ala Ser Gln Tyr Val Ser Leu Leu Ile Arg Asp
            100                 105                 110

Ser Gln Pro Ser Asp Ser Ala Thr Tyr Leu Cys Ala Val Asn Thr Pro
        115                 120                 125

Met Glu Tyr Gly Asn Lys Leu Val Phe Gly Ala Gly Thr Ile Leu Arg
    130                 135                 140

Val Lys Ser Tyr Ile Gln Asn Pro Asp Pro Ala Val Tyr Gln Leu Arg
145                 150                 155                 160

Asp Ser Lys Ser Ser Asp Lys Ser Val Cys Leu Phe Thr Asp Phe Asp
                165                 170                 175

Ser Gln Thr Asn Val Ser Gln Ser Lys Asp Ser Asp Val Tyr Ile Thr
            180                 185                 190

Asp Lys Thr Val Leu Asp Met Arg Ser Met Asp Phe Lys Ser Asn Ser
        195                 200                 205

Ala Val Ala Trp Ser Asn Lys Ser Asp Phe Ala Cys Ala Asn Ala Phe
    210                 215                 220

Asn Asn Ser Ile Ile Pro Glu Asp Thr Phe Phe Pro Ser Pro Glu Ser
225                 230                 235                 240

Ser Cys Asp Val Lys Leu Val Glu Lys Ser Phe Glu Thr Asp Thr Asn
                245                 250                 255

Leu Asn Phe Gln Asn Leu Ser Val Ile Gly Phe Arg Ile Leu Leu Leu
            260                 265                 270

Lys Val Ala Gly Phe Asn Leu Leu Met Thr Leu Arg Leu Trp Ser Ser
        275                 280                 285

<210> SEQ ID NO 4
<211> LENGTH: 314
<212> TYPE: PRT
<213> ORGANISM: Artificial Sequence
<220> FEATURE:
<223> OTHER INFORMATION: MART-1 (27-35) epitope-specific T cell receptor
      beta chain

<400> SEQUENCE: 4

Met Gly Thr Arg Leu Leu Cys Trp Val Val Leu Gly Phe Leu Gly Thr
1               5                   10                  15

Asp His Thr Gly Ala Gly Val Ser Gln Ser Pro Arg Tyr Lys Val Ala
            20                  25                  30
```

-continued

Lys Arg Gly Gln Asp Val Ala Leu Arg Cys Asp Pro Ile Ser Gly His
            35                  40                  45

Val Ser Leu Phe Trp Tyr Gln Gln Ala Leu Gly Gln Gly Pro Glu Phe
 50                  55                  60

Leu Thr Tyr Phe Gln Asn Glu Ala Gln Leu Asp Lys Ser Gly Leu Pro
 65                      70                  75                  80

Ser Asp Arg Phe Phe Ala Glu Arg Pro Glu Gly Ser Val Ser Thr Leu
                    85                  90                  95

Lys Ile Gln Arg Thr Gln Gln Glu Asp Ser Ala Val Tyr Leu Cys Ala
                100                 105                 110

Ser Ser Tyr Val Val Gly Leu Thr Tyr Asn Glu Gln Phe Phe Gly Pro
            115                 120                 125

Gly Thr Arg Leu Thr Val Leu Glu Asp Leu Lys Asn Val Phe Pro Pro
130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Tyr Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Glu Ser
            260                 265                 270

Tyr Gln Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
290                 295                 300

Ala Met Val Lys Arg Lys Asp Ser Arg Gly
305                 310

<210> SEQ ID NO 5
<211> LENGTH: 9
<212> TYPE: PRT
<213> ORGANISM: Artificial Sequence
<220> FEATURE:
<223> OTHER INFORMATION: MART-1 (27-35) epitope sequence

<400> SEQUENCE: 5

Ala Ala Gly Ile Gly Ile Leu Thr Val
1               5

<210> SEQ ID NO 6
<211> LENGTH: 1890
<212> TYPE: DNA
<213> ORGANISM: Artificial Sequence
<220> FEATURE:
<223> OTHER INFORMATION: DNA fragment of TCR alpha chain, P2A peptide
      and TCR beta chain

<400> SEQUENCE: 6
atgcctgcag gtcgacgatt aagcagtggt atcaacgcag agtacgggga gagttttact        60

```
agtgatcctg tggcttcagt tgagctgaga gtttggagcc aacagaagga ggtggagcag      120
aattctggac ccctcagtgt tccagaggga gccattgcct ctctcaactg cacttacagt      180
gaccgaggtt cccagtcctt cttctggtac agacaatatt ctgggaaaag ccctgagttg      240
ataatgttca tatactccaa tggtgacaaa gaagatggaa ggtttacagc acagctcaat      300
aaagccagcc agtatgtttc tctgctcatc agagactccc agcccagtga ttcagccacc      360
tacctctgtg ccgtgaacac ccccatgaaa tatggaaaca aactggtctt tggcgcagga      420
accattctga gagtcaagtc ctatatccag aaccctgacc ctgccgtgta ccagctgaga      480
gactctaaat ccagtgacaa gtctgtctgc ctattcaccg attttgattc tcaaacaaat      540
gtgtcacaaa gtaaggattc tgatgtgtat atcacagaca aaactgtgct agacatgagg      600
tctatggact tcaagagcaa cagtgctgtg gcctggagca caaatctga ctttgcatgt       660 gcaaacgcct tcaacaacag cattattcca gaagacacct tcttccccag cccagaaagt      720
tcctgtgatg tcaagctggt cgagaaaagc tttgaaacag atacgaacct aaactttcaa      780
aacctgtcag tgattgggtt ccgaatcctc ctcctgaaag tggccgggtt taatctgctc      840
atgacgctgc ggctgtggtc cagccgggcc aagcggtccg ggtccggagc caccaacttc      900
agcctgctga agcaggccgg cgacgtggag gagaaccccg gccccatggg caccaggctc      960
ctctgctggg tggtcctggg tttcctaggg acagatcaca caggtgctgg agtctcccag      1020
tcccctaggt acaaagtcgc aaagagagga caggatgtag ctctcaggtg tgatccaatt      1080
tcgggtcatg tatcccttt ttggtaccaa caggccctgg ggcaggggcc agagtttctg       1140
acttatttcc agaatgaagc tcaactagac aaatcggggc tgcccagtga tcgcttcttt      1200
gcagaaaggc ctgagggatc cgtctccact ctgaagatcc agcgcacaca gcaggaggac      1260
tccgccgtgt atctctgtgc cagcagctac gtagtgggac tgacctacaa tgagcagttc      1320
ttcgggccag ggacacggct caccgtgcta gaggacctga aaaacgtgtt cccacccgag      1380
gtcgctgtgt ttgagccatc agaagcagag atctcccaca cccaaaaggc cacactggtg      1440
tgcctggcca caggcttcta ccccgaccac gtggagctga gctggtgggt gaatgggaag      1500
gaggtgcaca gtggggtcag cacagacccg cagcccctca aggagcagcc cgccctcaat      1560
gactccagat actgcctgag cagccgcctg agggtctcgg ccaccttctg gcagaacccc      1620
cgcaaccact tccgctgtca agtccagttc tacgggctct cggagaatga cgagtggacc      1680
caggataggg ccaaacctgt cacccagatc gtcagcgccg aggcctgggg tagagcagac      1740
tgtggcttca cctccgagtc ttaccagcaa ggggtcctgt ctgccaccat cctctatgag      1800
atcttgctag ggaaggccac cttgtatgcc gtgctggtca gtgccctcgt gctgatggcc      1860
atggtcaaga gaaaggattc cagaggctag                                      1890
```

<210> SEQ ID NO 7
<211> LENGTH: 20
<212> TYPE: DNA
<213> ORGANISM: Artificial Sequence
<220> FEATURE:
<223> OTHER INFORMATION: Primer Outer of TCRA

<400> SEQUENCE: 7
gcagacagac ttgtcactgg                                                    20

<210> SEQ ID NO 8
<211> LENGTH: 29
<212> TYPE: DNA

```
<213> ORGANISM: Artificial Sequence
<220> FEATURE:
<223> OTHER INFORMATION: Primer Middle of TCRA

<400> SEQUENCE: 8
tggatttaga gtctctcagc tggtacacg                                   29

<210> SEQ ID NO 9
<211> LENGTH: 23
<212> TYPE: DNA
<213> ORGANISM: Artificial Sequence
<220> FEATURE:
<223> OTHER INFORMATION: Primer Inner of TCRA

<400> SEQUENCE: 9
ggtacacggc agggtcaggg ttc                                         23

<210> SEQ ID NO 10
<211> LENGTH: 21
<212> TYPE: DNA
<213> ORGANISM: Artificial Sequence
<220> FEATURE:
<223> OTHER INFORMATION: Primer Outer of TCRB

<400> SEQUENCE: 10
tggtcgggga agaagcctgt g                                           21

<210> SEQ ID NO 11
<211> LENGTH: 26
<212> TYPE: DNA
<213> ORGANISM: Artificial Sequence
<220> FEATURE:
<223> OTHER INFORMATION: Primer Middle of TCRB

<400> SEQUENCE: 11
tctgcttctg atggctcaaa cacagc                                      26

<210> SEQ ID NO 12
<211> LENGTH: 23
<212> TYPE: DNA
<213> ORGANISM: Artificial Sequence
<220> FEATURE:
<223> OTHER INFORMATION: Primer Inner of TCRB

<400> SEQUENCE: 12
ttctgatggc tcaaacacag cga                                         23
```